(12) United States Patent
Wang et al.

(10) Patent No.: US 12,094,596 B2
(45) Date of Patent: Sep. 17, 2024

(54) METHOD AND SYSTEM FOR ANATOMICAL LABELS GENERATION

(71) Applicant: SHENZHEN KEYA MEDICAL TECHNOLOGY CORPORATION, Shenzhen (CN)

(72) Inventors: Xin Wang, Seattle, WA (US); Youbing Yin, Kenmore, WA (US); Bin Kong, Charlotte, NC (US); Yi Lu, Seattle, WA (US); Xinyu Guo, Redmond, WA (US); Hao-Yu Yang, Seattle, WA (US); Junjie Bai, Seattle, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 399 days.

(21) Appl. No.: 17/726,039

(22) Filed: Apr. 21, 2022

(65) Prior Publication Data
US 2022/0344033 A1 Oct. 27, 2022

Related U.S. Application Data

(60) Provisional application No. 63/178,894, filed on Apr. 23, 2021.

(51) Int. Cl.
*G06V 10/82* (2022.01)
*G06N 3/045* (2023.01)
(Continued)

(52) U.S. Cl.
CPC ............. *G16H 30/40* (2018.01); *G06N 3/045* (2023.01); *G06V 10/82* (2022.01); *G06V 20/70* (2022.01)

(58) Field of Classification Search
CPC .......... G06V 10/82; G06V 20/70; G06N 7/01; G06T 2207/20084
See application file for complete search history.

(56) References Cited

U.S. PATENT DOCUMENTS 10,430,949 B1 * 10/2019 Wang ...................... G06N 3/084
2017/0245821 A1 * 8/2017 Itu ......................... A61B 8/5223
(Continued)

FOREIGN PATENT DOCUMENTS

CN 113192069 A * 7/2021

*Primary Examiner* — Ian L Lemieux
*Assistant Examiner* — Sebastian-Sy Vuchi Ngo
(74) *Attorney, Agent, or Firm* — Bayes PLLC (57) ABSTRACT

The present disclosure relates to a method and a system for generating anatomical labels of an anatomical structure. The method includes receiving an anatomical structure with an extracted centerline, or a medical image containing the anatomical structure with the extracted centerline; and predicting the anatomical labels of the anatomical structure based on the centerline of the anatomical structure, by utilizing a trained deep learning network. The deep learning network includes a branched network, a Graph Neural Network, a Recurrent Neural Network and a Probability Graph Model, which are connected sequentially in series. The branched network includes at least two branch networks in parallel. The method in the disclosure can automatically generate the anatomical labels of the whole anatomical structure in medical image end to end and provide high prediction accuracy and reliability.

20 Claims, 6 Drawing Sheets

(51) Int. Cl.
*G06V 20/70* (2022.01)
*G16H 30/40* (2018.01)

(56) References Cited

U.S. PATENT DOCUMENTS

| | | | |
|---|---|---|---|
| 2021/0057107 A1* | 2/2021 | Solomon | G06N 3/044 |
| 2022/0012890 A1* | 1/2022 | Wu | G06T 7/0012 |
| 2022/0172356 A1* | 6/2022 | Yang | G06V 10/30 |
| 2022/0301658 A1* | 9/2022 | Zamft | G16B 5/20 |

* cited by examiner

METHOD AND SYSTEM FOR ANATOMICAL LABELS GENERATION

CROSS REFERENCE TO RELATED APPLICATION

This application is based on and claims the priority of U.S. Provisional Application No. 63/178,894, filed Apr. 23, 2021, which is incorporated herein by reference in its entirety.

TECHNICAL FIELD

The present disclosure relates to the technical field of processing and analyzing medical data and medical image, and more specifically, to a method and system for generating anatomical labels of an anatomical structure captured in a medical image.

BACKGROUND

Automatically identifying and assigning correct anatomical labels to anatomical structures facilitates the precise diagnosis. However, the morphology and topology of these anatomical structures vary widely individually. Therefore, the challenge of automatic anatomical structure labeling arises from the large individual variability of coronary anatomy, for example, especially some of the secondary branches emerging from the main branches.

Some of prior art estimate labels by using learning-based methods. However, these previous methods are not reliable to deal with the scene of large individual variability as either the model is not end-to-end or the model requires pre-defined features. Besides, the previous methods do not model for the correlation of each label. The above two points greatly limit the performance such as accuracy and robustness of dealing with the scene of large individual variability.

SUMMARY

Certain embodiments may provide a method and a system for generating anatomical labels of the anatomical structure. Such a method and system may automatically generate anatomical labels of the whole anatomical structure in medical images in an end-to-end manner, by utilizing a trained deep learning network. The method and system may also provide strong robustness, higher prediction accuracy and reliability despite of a large individual variability in coronary anatomy. The disclosed embodiments are provided to solve at least the technical problems mentioned above.

According to a first aspect of the present disclosure, there is provided a method for generating anatomical labels of an anatomical structure. The method begins with receiving an anatomical structure with an extracted centerline, or a medical image containing the anatomical structure with the extracted centerline. Next, the method includes predicting the anatomical labels of the anatomical structure based on the centerline of the anatomical structure, by utilizing a trained deep learning network/. The deep learning network includes a branched network, a Graph Neural Network, a Recurrent Neural Network and a Probability Graph Model which are connected sequentially in series. The branched network includes at least two branch networks in parallel.

According to a second aspect of the present disclosure, there is provided a system for generating anatomical labels of the anatomical structure. The system includes an interface configured to receive an anatomical structure with an extracted centerline, or a medical image containing the anatomical structure with the extracted centerline. The system further includes at least one processor configured to predict the anatomical labels of the anatomical structure based on the centerline of the anatomical structure, by utilizing a trained deep learning network. The deep learning network includes a branched network, a Graph Neural Network, a Recurrent Neural Network and a Probability Graph Model which are connected sequentially in series. The branched network includes at least two branch networks in parallel.

According to the third aspect of the present disclosure, there is provided a non-transitory computer-readable storage medium, with computer-executable instructions stored thereon. The instructions, when executed by a processor, cause the processor to perform a method for generating anatomical labels of the anatomical structure by utilizing a computer, corresponding to the method described above.

Embodiment disclosed herein provide an end-to-end precise prediction of the anatomical structure, based on the centerline graph constructed by sampling points of the centerline of the anatomical structure, by considering various features such as the geometric feature and the image feature of the centerline graph, utilizing multiple branch networks provided in parallel and implementing a joint embedding of multiple features by a Graph Neural Network. They enable a more reasonable and robust division of the whole anatomical structure from the perspective of global optimization by modeling for the relationship between anatomical labels, utilizing a Probability Graph Model. Therefore, the methods in the present disclosure can realize automatic end-to-end prediction of the anatomical labels of the anatomical structure with higher accuracy and robustness, and are also more suitable for the prediction of the anatomical labels of the anatomical structures with greater individual variability. Accordingly, the diagnosis accuracy and diagnosis efficiency of doctors may be improved.

The above general description and the following detailed description are exemplary and explanatory only, and are not intended to limit the claimed invention.

BRIEF DESCRIPTION OF THE DRAWINGS

In the drawings, which are not necessarily drawn to scale, like reference numerals may describe similar components in various views. Like reference numerals having letter suffixes or different letter suffixes may represent different instances of similar components. The drawings illustrate generally, by way of example, but not by way of limitation, various embodiments, and together with the description and claims, serve to explain the disclosed embodiments. Such embodiments are demonstrative and not intended to be exhaustive or exclusive embodiments of the present method, device, system and non-transitory computer readable medium with instructions for implementing the method.

DETAILED DESCRIPTION

In order to enable those skilled in the art to understand the present invention better, the embodiments of the present invention will be described in detailed below with reference to the drawings, but not as a limitation of the present invention.

Figure 1:
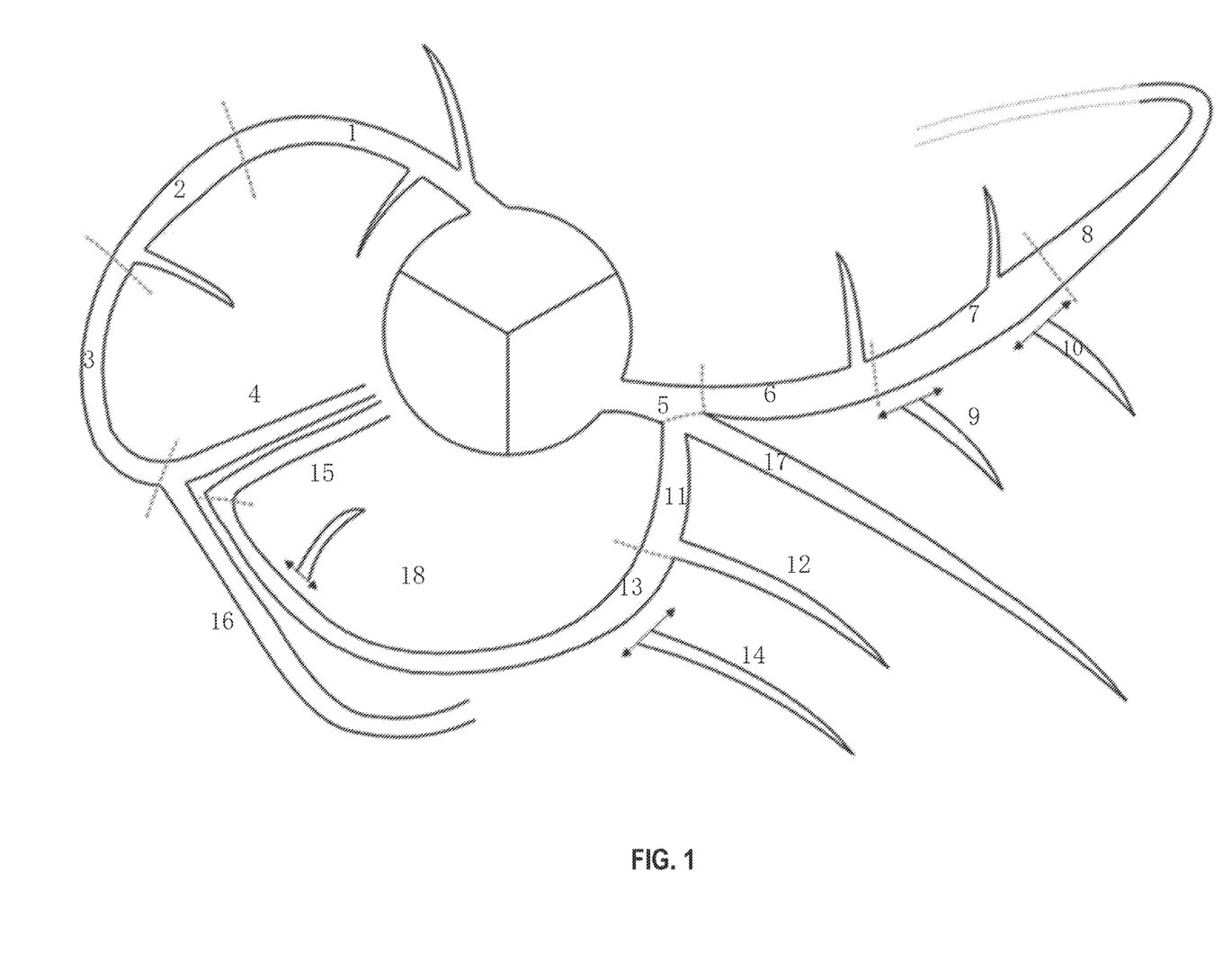
FIG. 1 illustrates a schematic diagram of exemplary anatomical labels of the coronary artery, according to an embodiment of the present disclosure.

FIG. 1 illustrates a schematic diagram of exemplary anatomical labels of the coronary artery according to the embodiment of the present disclosure. It is to be noted that the technical scheme of the present disclosure will be explained below by taking the anatomical structure as the coronary artery or the anatomical structure contained in the acquired medical image as coronary artery as an example, but the present disclosure is not limited to this.

Coronary artery is the artery that supplies blood to the heart. It originates from the aortic sinus at the root of the aorta and is divided into left and right branches and runs on the surface of the heart. According to Schlesinger's classification principle, the distribution of the coronary artery may be divided into right dominant type, balanced type and left dominant type. Different dominant types of the coronary artery may contain different anatomical structures, and there are many rules for labeling anatomical structures. For example, according to the classification of American heart association (AHA), the coronary arteries may be roughly divided into 15 segments, that is, 15 types of the anatomical labels. FIG. 1 is a specific manner of anatomical labeling of coronary arteries on the basis of AHA classification. The rules for segmenting and labeling the anatomical structure of coronary arteries are shown in Table 1.

TABLE 1

Anatomical labels of coronary artery and its labeling rules in FIG. 1

| Anatomical labels | Labeling rules |
| --- | --- |
| 1. pRCA: Proximal right coronary artery (RCA) | Ostium of the RCA to one-half the distance to the acute margin of heart coronary artery (RCA) |
| 2. mRCA: Middle RCA | End of proximal RCA to the acute margin of heart |
| 3. dRCA: Distal RCA | End of mid RCA to origin of the PDA (posterior descending artery) |
| 4. R-PDA: PDA-R | PDA from RCA |
| LAD branch: 5-6-7-8 | |
| 5. LM: Left main (LM) | Ostium of LM to bifurcation of LAD(left anterior descending artery)and LCx(left circumflex artery) |
| 6. pLAD: Proximal LAD | End of LM to the first large septal or D1(first diagonal; >1.5 mm in size) whichever is most proximal |
| 7. mLAD: Mid LAD | End of proximal LAD to one-half the distance to the apex |
| 8. dLAD: Distal LAD | End of mid LAD to end of LAD |
| D branch: 9, 10 | |

TABLE 1-continued

Anatomical labels of coronary artery and its labeling rules in FIG. 1

| Anatomical labels | Labeling rules |
| --- | --- |
| 9. D1: First diagonal branch | First diagonal branch D1 |
| 10. D2: Second diagonal branch | Second diagonal branch D2 |
| 11. pCx: Proximal LCx | End of LM to the origin of the OM1 (first obtuse marginal) |
| 12. OM1: OM1 | First OM1 traversing the lateral wall of the left ventricle |
| 13. LCx: Middle and distal LCx | Traveling in the atriove ntricular groove, distal to the OM1 branch to the end of the vessel or origin of the L-PDA(left PDA) |
| 14. OM2: Second marginal OM2 | Second marginal OM2 |
| 15. PDA-L: L-PDA | PDA from LCx |
| 16. PLB-R: R-PLB | PLB from RCA |
| 17. RI: Ramus intermedius | Vessel originating from the left main between the LAD and LCx in case of a trifurcation |
| 18. PLB-L: L-PLB | PLB from LCx |

The anatomical structure of the coronary artery shown in FIG. 1 may vary greatly in different individuals. For example, the 14th segment in the drawing, that is the second marginal OM2, may be absent in some individuals, and so on, In addition, the labeling rules of the anatomical labels can also include the relationship between anatomical labels. Taking Table 1 as an example, LAD branch is connected by segment 5 (LM: Left Main)—segment 6 (pLAD: Proximal LAD)—segment 7 (mLAD: Mid LAD)—segment 8 (dLAD: Distal LAD). D branch includes segment 9 (D1: First diagonal branch) and segment 10 (D2; Second diagonal branch), while segment 9 originated from segment 6 or 7, and segment 10 originated from segment 8 or the transition part of segment 7 and 8. In other embodiments, the D branch may also include segment 9a (D1a: First diagonal a, not shown) and segment 10a (D2a: Second diagonal a, not shown), etc. In this case, segment 9a may be additional first diagonal originating from segment 6 or 7, before segment 8 (the distal segment of the anterior descending branch). In some embodiments, the method according to the present disclosure can comprehensively consider the above bidirectional constraint relationship between anatomical labels when determining the anatomical labels of various parts of the anatomical structure, so that the prediction of the anatomical labels of the whole anatomical structure may be more accurate and reliable from the perspective of global optimization.

It is to be noted that the anatomical structure according to the embodiment of the present disclosure is not necessarily a coronary artery, but also any vessel, respiratory tract, mammary duct, etc., especially an anatomical structure with a multi-branched tree, which is not listed here.

Figure 2:
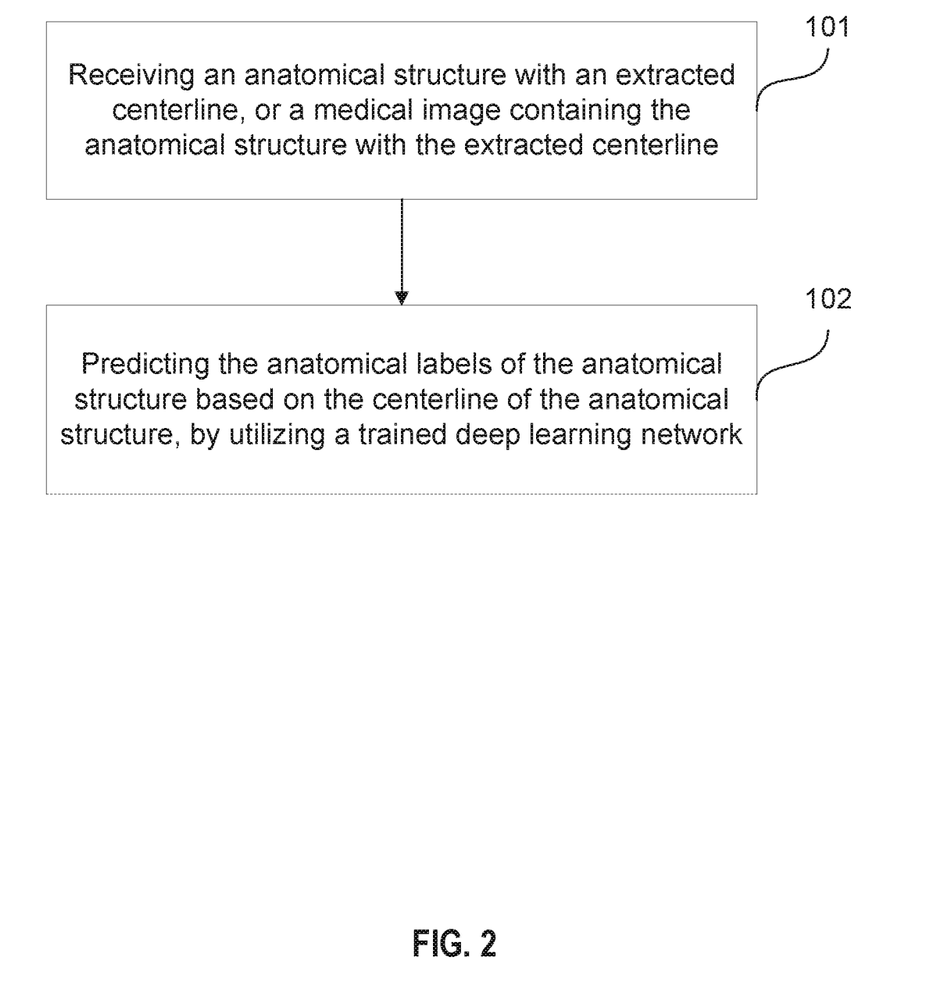
FIG. 2 illustrates a flowchart of a method for generating anatomical labels of the anatomical structure, according to an embodiment of the present disclosure.

FIG. 2 illustrates a flowchart of a method for generating the anatomical labels of the anatomical structure, according to the embodiment of the present disclosure.

First, at step S101, an anatomical structure with an extracted centerline or a medical image containing the anatomical structure with the extracted centerline may be received. In some embodiments, it is also possible to receive an anatomical structure without the extracted centerline or a medical image containing the anatomical structure without the extracted centerline, and extract the centerline of the anatomical structure by using any algorithm for extract the centerline, at the same time, some useful data information, such as the segmentation mask, may be extracted together. The above process for centerline extracting may be implemented automatically, semi-automatically, or manually, and any suitable algorithm or method may be adopted. The present disclosure is not limited to this.

Next, at step S102, the anatomical labels of the anatomical structure may be predicted based on the centerline of the anatomical structure received or extracted at step 101, by utilizing a trained deep learning network. In some embodiments, the above deep learning network may include a branched network including at least two branch networks, a Graph Neural Network, a Recurrent Neural Network and a Probability Graph Model. These networks are connected sequentially in series, with the at least two branch networks within the branched network in parallel.

In some embodiments, when predicting the anatomical labels based on the centerline of the anatomical structure, a graph representation of the centerline of the anatomical structure may be first constructed based on the centerline of the anatomical structure. For example, it is possible to sample for the centerline and take each sampling point as a node (hereinafter represented by V) of a centerline graph (hereinafter represented by G) of the centerline, and take a line segment on the centerline connecting each pair of adjacent nodes as an edge (hereinafter represented by E) of the centerline graph.

In some embodiments, for each node $v_i$ in V, the associated physic coordinates, image patches and any other useful information may be extracted as the representation of the node $v_i$.

In some embodiments, for example, the edge $e_i$ in E may be represented as one undirected edge or two directed edges, where the directed edge may bring more information than undirected edges, especially may be used to represent the bidirectional constraint relationship between two nodes connected by $e_i$. For example, in the coronary artery tree structure, information can be propagated from the root of the tree to the terminal, and it can also be propagated from the opposite direction (from terminal to the root).

Based on the settings of the set V of nodes and the set E of edges, the centerline graph G can be expressed as: G=(V, E), where the node $v_i \in V$ in V corresponds to the feature vectors or embedding of the points on the centerline, and $e_j \in E$ corresponds to the directed or undirected edges between the points. i∈[1, ..., N], j∈[1, ... ,N−1], where N is the node number of the centerline graph G.

Once modeling the centerline graph of the anatomical structure has been finished, it is possible to predict the anatomical labels of the anatomical structure based on the centerline graph G, by utilizing the trained deep learning network. The specific procedure will be described in detail with reference to FIG. 3.

The method for determining the anatomical labels in the disclosed embodiment takes the anatomical structure and the medical image containing the anatomical structure as input, and realizes end-to-end prediction of the anatomical labels by using multiple of deep learning networks such as deep neural networks combined in parallel and in series, which can learn the anatomical feature for identifying the essence of the anatomical structure such as arteries without any artificially defined standards and features. Compared with the prior art, the pre-defined discrete feature extraction module s no longer needed, instead, from the perspective of global joint optimization, the above deep learning network is learned and used as a whole, and the anatomical labels of each part in the anatomical structure may be directly output at the output end of the deep learning network. With the increase of the amount of training data, the performance of the deep learning network in terms of accuracy and robustness will also be improved.

Figure 3:
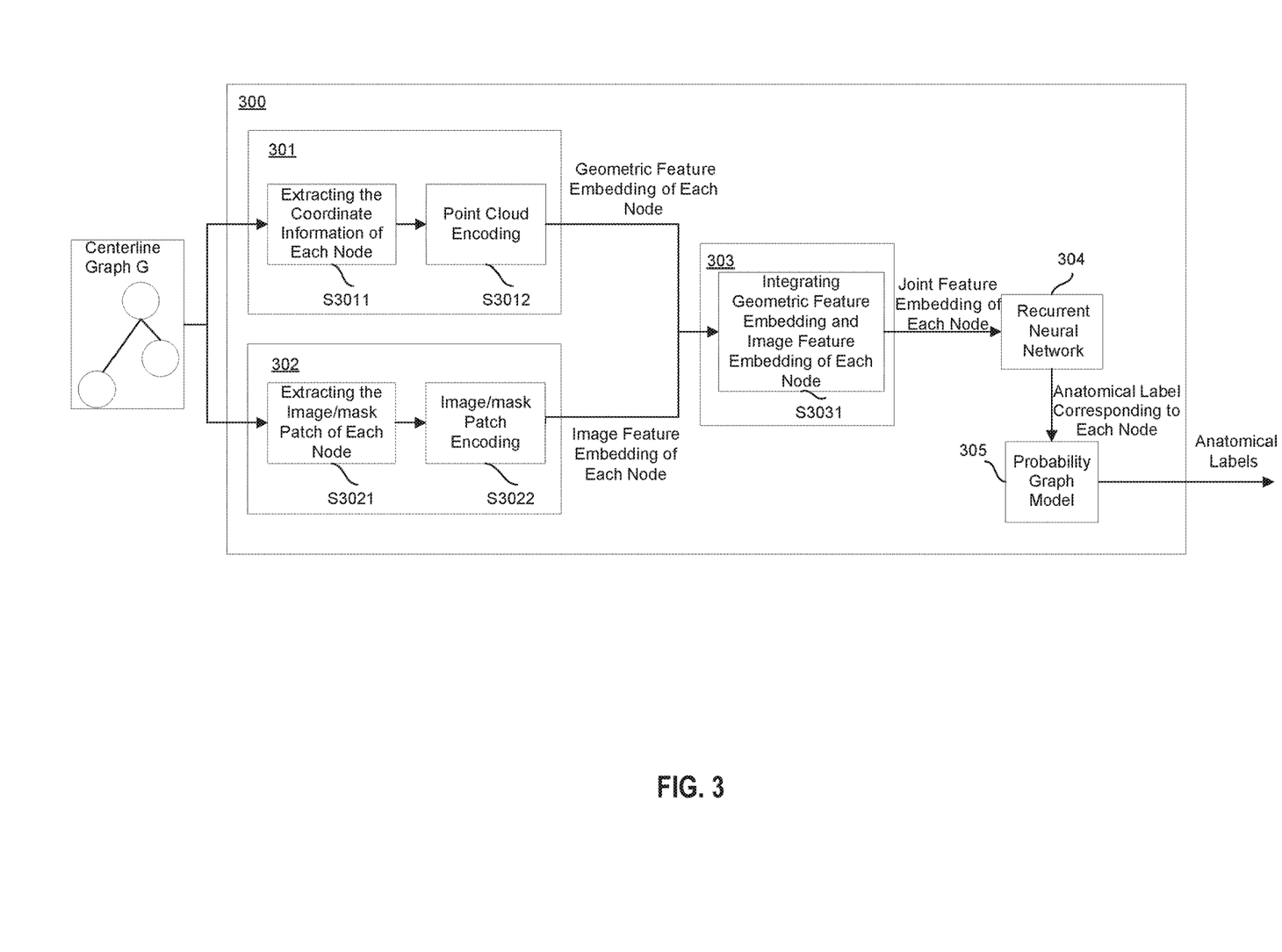
FIG. 3 illustrates a schematic diagram of a procedure of predicting anatomical labels by utilizing a trained deep learning network, according to an embodiment of the present disclosure.

In some embodiments, first, the first branch network 301 can extract the coordinate information of each node $v_i$ based on the centerline graph G in step S3011, and use the extracted coordinate information as the input for embedding the geometric feature. Since the coordinate information may be used as a point cloud, in step S3012, for example, any point cloud network such as PointNet, PointNet++ may be used to encode the coordinate information and generate the geometric feature embedding of each node. The present disclosure is not particularly limited to the point cloud network used by the first branch network 301, as long as the geometric feature embedding of each node may be generated based on the coordinate information of each node in the centerline graph G.

In some embodiments, there may be one or more other branch networks provided in parallel with the above first branch network 301, such as the second branch network 302 shown in FIG. 3. In some embodiments, the second branch network 302 may synchronize with the first branch network 301, and in step S3021, extract the 2D/3D image patch or the mask patch corresponding to each node $v_i$ based on the center line graph G, and use the extracted image patch/mask patch as input for embedding the image feature. In some embodiments, for example, the optimized window width may be selected according to different anatomical parts, so as to complete the extraction of the image patch/mask patch, etc. The present disclosure is not specifically limit to this. In some embodiments, for example, in step S3022, the second branch network 302 may adopt any deep learning network based on CNN(Convolutional Neural Network), GCN (Graph Convolutional Neural Network), RNN(Recurrent Neural Network) or MLP(Multilayer perceptron), such as ResNet, VGG, etc., encode the image/mask information of each node and generate the image/mask feature embedding of each node.

As an example only, in case of the second branch network 302 selects GCN as the deep learning network for embedding the image feature, GCN can generalize the architecture of CNN to non-Euclidean domains such as the graph. The graph convolution defines convolutions directly on the graph, operating on spatially close neighbors. Formally, Z=GCN(X, A), where X ∈RN×C, is the input, N is the node number, and C is the dimension of the feature embedding, A is an adjacent matrix to denote if there are edges between nodes, in the embodiment of the present disclosure, A may be determined by the centerline graph, Z is the output of the GCN. It should be note that other common methods used in CNN can also be used in GCN, such as skipping connection or attention. In addition, in some embodiments, the second branch network 302 can also select other advanced GNN variants, for example, gated GNN method. In other embodiments, it can also use the gate mechanism like GRU or LSTM in the propagation step to improve the long-terra propagation of information across the graph structure. For example, if the edges of the graph are directional, by using a gate mechanism, the parent node can selectively incorporate information from each child node. More specifically, each graph unit (could be a GRU or LSTM unit) includes input and output gates, a memory cell, and a hidden state. Instead of a single forget gate, each graph unit includes one forget gate for each child node. The above graph unit could be any RNN unit such as LSTM, GRU, CLSTM, CGRU, etc.

As mentioned above, the present disclosure is not particularly limited to the deep learning network and feature embedding method used by the second branch network 302, as long as the image information coding can be realized, and the image/mask feature embedding of each node can be generated based on the image patch/mask patch corresponding to each node in the centerline graph G.

After obtaining the geometric feature embedding and the image feature embedding of each node of the centerline graph G by the first branch network 301 and the second branch network 302 respectively, next, the Graph Neural Network 303 may be used to integrate the geometric feature embedding and the image feature embedding of each node in step S3031 to obtain the joint feature embedding of each node. The method of integrating two or more feature embeddings is not specifically limited here, and it may simply concatenate the feature embedding of each branch, or combining the feature embeddings of multiple branches according to the predetermined weight to generate the joint feature embedding, which are not listed here.

Next, the joint feature embedding of each node output by the Graph Neural Network 303 can be the input of the Recurrent Neural Network 304, and the Recurrent Neural Network 304 can be used to generate the anatomical label corresponding to each node in the centerline graph G of the anatomical structure by utilizing the Recurrent Neural Network 304. The above Recurrent Neural Network 304 may adopt any one of LSTM, GRU, CLSTM, CGRU, or a variation based on it. The present disclosure is not limited to this.

Further, the cell division of the whole anatomical structure and the anatomical label corresponding to each cell may be generated, for example, by induction or clustering, based on the anatomical label corresponding to each node in the centerline graph G and according to the anatomical label corresponding to each node by utilizing the Probability Graph Model 305. The above Probability Graph Model may also be other models besides CRF, such as MRF (Markov Random Field) or high-order CRF, or other variations based on this. The present disclosure is not limited to this.

According to the method for determining the anatomical labels in the embodiment of the present disclosure as shown in FIG. 3, the geometric feature or the image feature in the centerline graph constructed based on the anatomical structure not only may be considered independently, but also may be considered jointly being integrated into a joint feature embedding vector by using GNN network. The joint feature embedding vector may improve the prediction accuracy of the deep learning network, regardless the joint feature embedding vector is generated by simple concatenating or by weighted fusion.

In some embodiments, the centerline may be divided into a plurality of cells at first, and after the joint feature embedding of each node is generated by utilizing the Graph Neural Network, performing cell level average pooling for the joint feature embedding of each node based on the divided cells of the centerline to generate cell level features. Then, generating the cell level anatomical labels of the centerline graph based on the cell level features, by utilizing the Recurrent Neural Network. Finally, generating the anatomical labels of the anatomical structure based on the cell level anatomical labels, by utilizing the Probability Graph Model.

Figure 4:
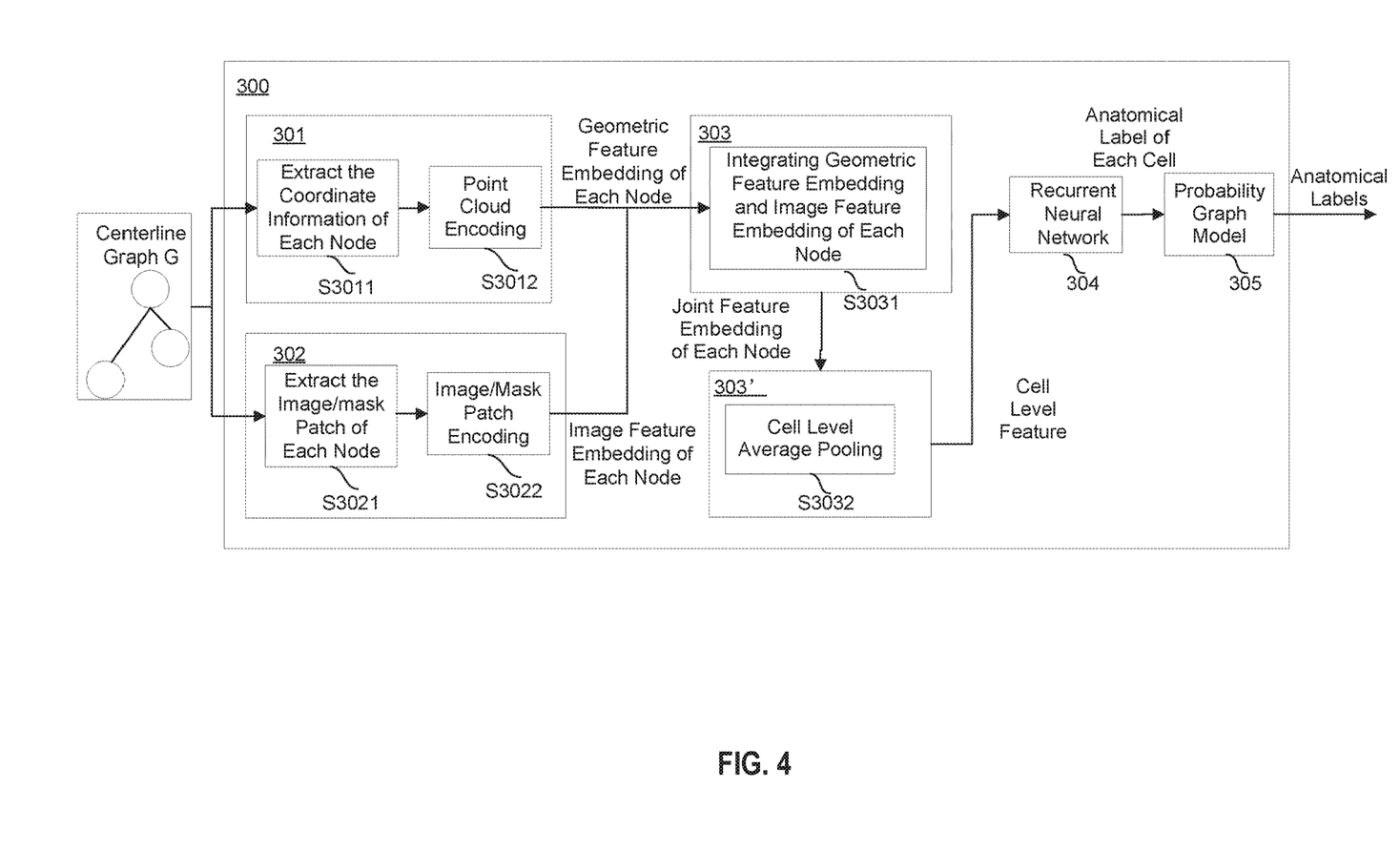
FIG. 4 illustrates a schematic diagram of another procedure of predicting anatomical labels by utilizing a trained deep learning network, according to an embodiment of the present disclosure.

FIG. 4 illustrates a schematic diagram of another procedure of predicting the anatomical labels by utilizing the trained deep learning network according to an embodiment of the present disclosure. FIG. 4 is similar to FIG. 3 in that the deep learning network 300 includes components of the first branch network 301, the second branch network 302, the Graph Neural Network 303, the Recurrent Neural Network 304 and the Probability Graph Model 305, and the operations and steps in each component are basically the same. FIG. 4 is different from FIG. 3 in that, after the Graph Neural Network 303 integrates the geometric features and image features of each node and outputs the joint feature embedding of each node in step S3031, it is not directly sent to the Recurrent Neural Network 304, but a pooling unit 303' is used, and in step S3032, cell level average pooling is performed for the joint feature embedding of each node.

In some embodiments, in order to obtain more accurate anatomical labels prediction results when sampling the centerline of the anatomical structure, the sampling is usually denser, the number of nodes is larger, and the correlation between adjacent nodes is larger. In anatomical structure such as vessel, the vessel between two bifurcations usually belong to the same vessel branch, that is, have the same anatomical labels. Therefore, it can be set that in case of the anatomical structure is a vessel, each cell of the centerline is the vessel branch between two bifurcations. The centerline may be divided into cells manually, automatically, or semi-automatically, and the present disclosure is not limit to this.

Taking the coronary artery shown in FIG. I as an example, the vessel branch between bifurcations may be taken as basic cell along the centerline of the coronary artery, and performing cell level average pooling for the centerline graph with the joint feature embedding. The cell level features output by the pooling unit 303' are input to the Recurrent Neural Network 304 after cell level average pooling. At this time, the Recurrent Neural Network 304 will output the anatomical label sequence of each cell based on the cell level features, which is different from FIG. 3.

As shown in the previous FIG. 1 and Table 1, D branches such as D1 and D2 are located on the LAD branch consisting of 5-6-7-8. That is to say, for structured labeling tasks, it is beneficial to consider the correlations between labels in neighborhoods and the whole structure and jointly decode the best structure of labels for a given input structure. Therefore, in some embodiments, the Probability Graph Model (PGM) such as the Conditional Random Field (CRF) may be used to jointly model the correlation of the labels, instead of decoding the anatomical labels of each cell independently, so that more reasonable and accurate anatomical labels may be obtained from the perspective of the whole anatomical structure.

In some cases, the anatomical structure may change greatly from individual to individual. Using the method of the embodiment of the present disclosure to model the relationship between the anatomical labels may deal with this change of individuals in a large degree. Under the constraints of the relationship between anatomical labels, the method according to the present disclosure can make accurate and robust predictions of the anatomical labels in the whole anatomical structure, such as the whole blood vessel tree, by making use of these constraints, thereby helping doctors to accurately and efficiently respond to individual differences and make accurate and reliable diagnosis for different patients.

The embodiment according to the present disclosure also provides a device for determining the anatomical labels of the anatomical structure by utilizing the computer, which includes a storage, at least one processor, and computer-executable instructions stored on the storage and ran on the at least one processor, wherein the at least one processor executes the steps of the method for determining the anatomical labels of the anatomical structure by utilizing the computer described in the previous embodiments.

The embodiment of the present disclosure also provides a system for determining the anatomical labels of the anatomical structure by utilizing the computer. The system includes an interface, a model training device and an image processing device, wherein the interface is used receive an anatomical structure with an extracted centerline, or a medical image containing the anatomical structure with the extracted centerline required in the training phase, and/or receive the anatomical structure with the extracted centerline, or the medical image containing the anatomical structure with the extracted centerline of which the anatomical labels are to be predicted in the prediction phase.

The system for determining the anatomical labels of the anatomical structure by utilizing the computer also includes the model training device, which is used to train the deep learning network in the method for determining the anatomical labels of the anatomical structure by utilizing the computer described in the previous embodiments in the training phase.

The system for determining the anatomical labels of the anatomical structure by utilizing the computer also includes the image processing device, which is used to perform the steps of the method for determining the anatomical labels of the anatomical structure by utilizing the computer described in the previous embodiments in the prediction phase.

Figure 5:
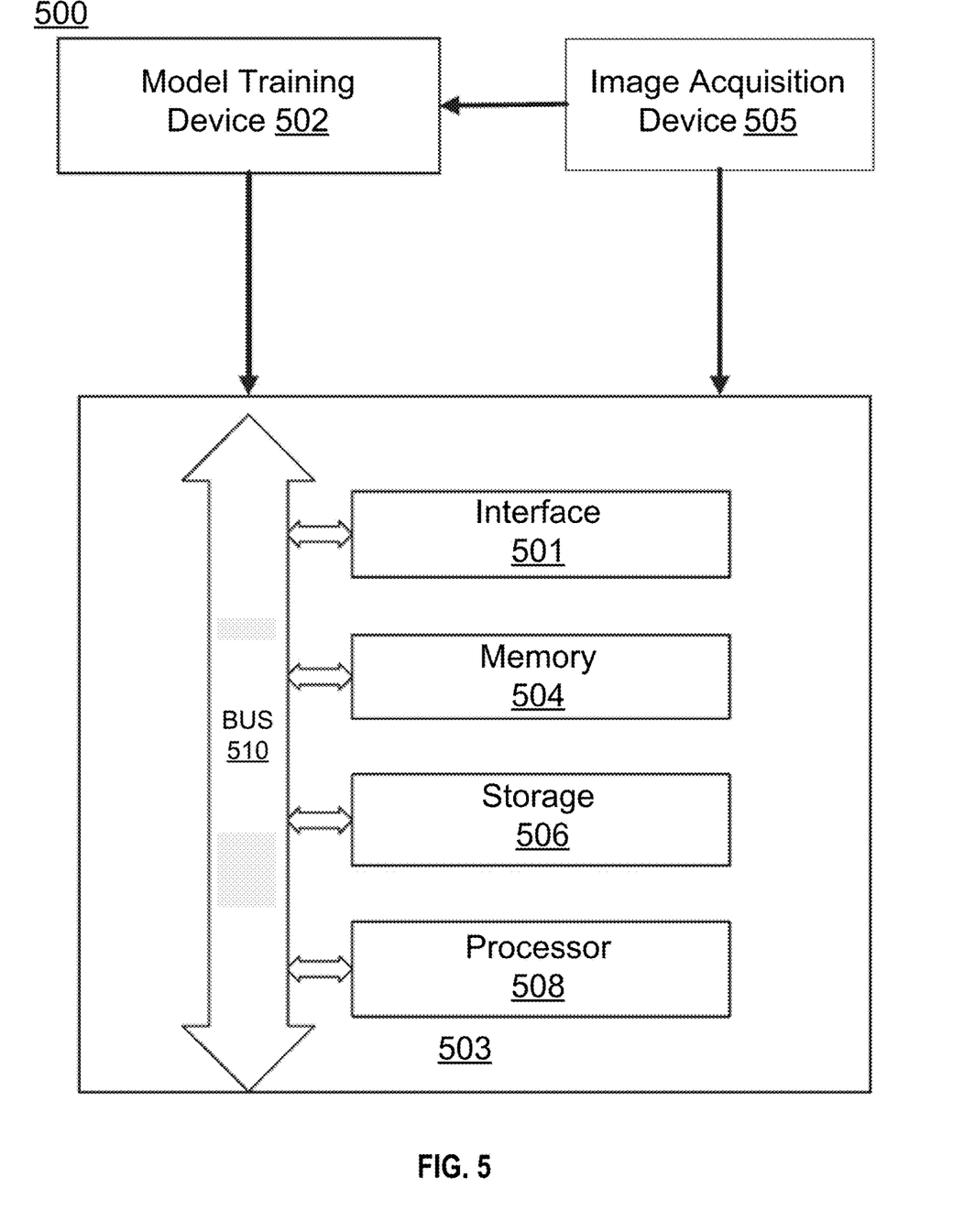
FIG. 5 illustrates a schematic block diagram of a system for generating anatomical labels of the anatomical structure, according to an embodiment of the present disclosure.

FIG. 5 illustrates a schematic block diagram of the system for determining the anatomical labels of the anatomical structure by utilizing the computer according to the system of the embodiment of the present disclosure. The system 500 may include the model training device 502 configured to train the deep learning network according to the embodiment of the present disclosure in the training phase, and the image processing device 503 configured to perform the anatomical label prediction task in the prediction phase. In some embodiments, the model training device 502 and the image processing device 503 may be within the same computer or processing device.

In some embodiments, the image processing device 503 may be a special-purpose computer or a general-purpose computer. For example, the image processing device 503 may be a customized computer that performs image acquisition or image processing tasks in a hospital or a server arranged in the cloud. The image processing device 503 may include a communication interface 501, a memory 504, a storage 506, a processor 508, and a bus 510. The interface 501, the memory 504, the storage 506, and the processor 508 are connected to the bus 510 and communicate with each other through the bus 510.

The communication interface 501 may include a network cable connector, a cable connector, a serial connector, a USB connector, a parallel connector, a high-speed data transmission adapter such as optical fiber, USB 3.0, Thunder, etc., a wireless network adapter such as a WiFi adapter, a telecommunications (3G, 4G/LTE, etc.) adapter, etc. In some embodiments, the interface 501 receives the medical image containing the anatomical structure from the image acquisition device 505. In some embodiments, the interface 501 also receives the trained deep learning network model from the model training device 502.

The image acquisition device 505 can acquire images in any imaging form in functional MRI (such as fMRI, DCE-MRI and diffusion MRI), cone-beam computed tomography (CBCT), spiral CT, positron emission tomography (PET), single photon emission computed tomography (SPECT), X-ray imaging, optical tomography, fluorescence imaging, ultrasound imaging and radiation field imaging, etc. or their combination. The disclosed method may be performed by a system that uses the acquired image to make anatomical label prediction.

The memory 504/storage 506 may be a non-transitory computer-readable medium, such as read only memory (ROM), random access memory (RAM), phase change random access memory (PRAM), static random access memory (SRAM), dynamic random access memory (DRAM), electrically erasable programmable read only memory (EEPROM), other types of random access memory (RAMs), flash disk or other forms of flash memory, cache, register, static memory, compact disc read-only memory (CD-ROM), digital versatile disc (DVD) or other optical storage, magnetic tape or other magnetic storage devices, or any other non-transitory medium that may be used to store information or instructions that may be accessed by the computer device, etc.

In some embodiments, the memory 504 may store the trained deep learning model and data, such as the centerline graph generated when the computer program is executed. In some embodiments, the storage 506 may store computer-executable instructions, such as one or more image processing programs.

The processor 508 may be a processing device including one or more general-purpose processing devices, such as a microprocessor, a central processing unit (CPU), a graphics processing unit (GM), etc. More specifically, the processor may be a complex instruction set computing (CISC) microprocessor, a reduced instruction set computing (RISC) microprocessor, a very long instruction word (VLIW) microprocessor, a processor running other instruction sets, or a processor running a combination of instruction sets. The processor can also be one or more special processing devices, such as application specific integrated circuit (ASIC), field programmable gate array (FPGA), digital signal processor (DSP), system on chip (SoC), etc. The processor 508 may be communicatively coupled to the storage 506 and configured to execute computer-executable instructions stored thereon.

The model training device 502 may be realized by hardware specially programmed by software that executes training processing. For example, the model training device 502 may include the same processor and non-transitory computer readable medium as the image processing device 503. The processor may be trained by executing the instructions of the training process stored in the computer-readable medium. The model training device 502 may also include input and output interfaces to communicate with a training database, a network, and/or a user interface. The user interface may be used to select the training data set, adjust one or more parameters of the training process, select or modify the framework of the learning model, and/or manually or semi-automatically provide the prediction results related to the anatomical structure in the trained image.

Figure 6:
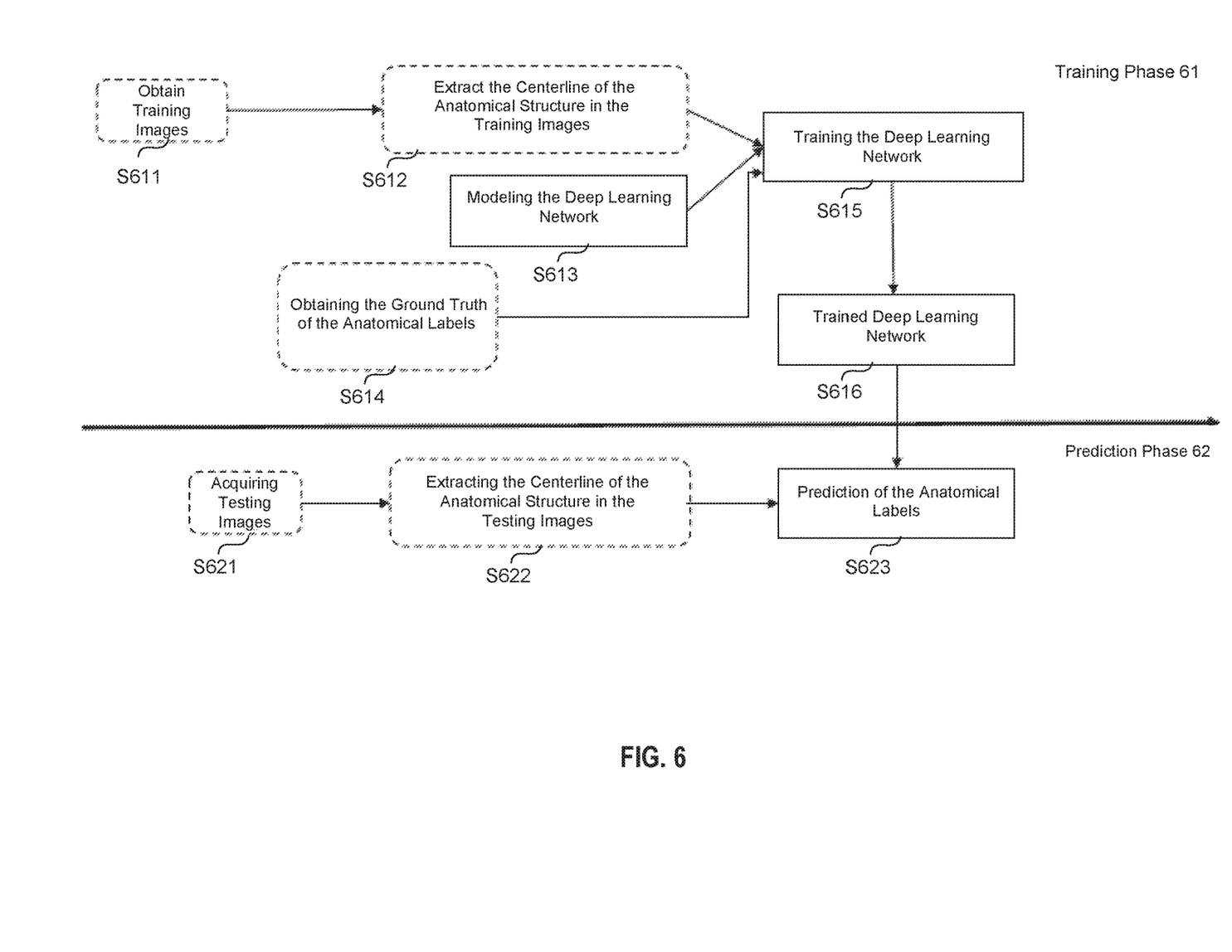
FIG. 6 illustrates a schematic workflow diagram of a system for generating anatomical labels of the anatomical structure, according to an embodiment of the present disclosure.

FIG. 6 is a schematic workflow diagram of the system for determining the anatomical labels of the anatomical structure by utilizing the computer according to an embodiment of the present disclosure.

As shown in FIG. 6, the workflow of the system for determining the anatomical labels of the anatomical structure by utilizing the computer according to the embodiment of the present disclosure may be divided into the training phase and the prediction phase, and the specific workflow is as follows:

In some embodiments, the training phase 61 is an off-line process. At this phase, first, the training image may be obtained in step S611, for example, the medical image containing the anatomical structure with or without the extracted centerline. In case of the centerline of the anatomical structure is not extracted, any applicable centerline extraction algorithm may be used to extract the centerline of the anatomical structure in the training image in step S612. Next, in step S613, the deep learning network to be trained may be modeled. The deep learning network is composed of at least two branch networks, the Graph Neural Network, the Recurrent Neural Network and the Probability Graph Model which is connected sequential in series, wherein the at least two branch networks are provided in parallel. In step S613, the image patch/mask patch and coordinates and other data information corresponding to each sampling point may be automatically extracted from the centerline by using the graph representation algorithm, create the centerline graph of the anatomical structure, and embed the feature of each node in the centerline graph. In the training phase, the ground truth of the anatomical labels may be obtained in step S614, or at this phase, the system assembles a database of anatomical structure training data labeled with the ground truth. Next, in step S615, the modeled deep learning network may be trained based on the centerline graph after feature embedding and the ground truth of the anatomical labels, and the trained deep learning network may be obtained in step S616. When training the end-to-end deep learning network model, gradient-based methods (such as SGD, Adam, et ay he used to optimize the objective function J relative to all parameters on the training data set. The parameter ($\theta$) of the deep learning network model may be optimized by minimizing the mean square deviation between the ground truth y and the predicted value output $\hat{y}$ of each node on the centerline graph. Especially, the parameter ($\theta$) may be optimized for the training set D to minimize the objective function J, where J may be any classification loss or AUC loss.

The prediction phase 62 may be an online process. In some embodiments, first, in step S621, a new test image of the anatomical labels to be predicted may be received, which should include the anatomical structure with or without the extracted centerline. In case of the centerline of the anatomical structure in the received test image is not extracted, the centerline of the anatomical structure in the test image may be extracted in step S622. Then, in step S623, the anatomical labels of the whole anatomical structure in the new test image may be calculated by utilizing the deep learning network trained in the training phase 61.

Various modifications and changes can be made to the method, device and system of the present disclosure. Other embodiments can be derived by those skilled in the art in view of the description and practice of the disclosed system and related methods. Each claim of the present disclosure can be understood as an independent embodiment, and any combination between them can also be used as an embodiment of the present disclosure, and these embodiments are deemed to be included in the present disclosure.

The examples merely regarded as exemplary only, and the true scope is indicated by the appended claims and their equivalents.

What is claimed is:

1. A computer-implemented method for generating anatomical labels of an anatomical structure, comprising:
   receiving an anatomical structure with an extracted centerline, or a medical image containing the anatomical structure with the extracted centerline; and
   predicting, by at least one processor, the anatomical labels of the anatomical structure based on the centerline of the anatomical structure, by utilizing a trained deep learning network, wherein the deep learning network comprises a branched network, a Graph Neural Network, a Recurrent Neural Network and a Probability Graph Model, which are connected sequentially in series, wherein the branched network comprises at least two branch networks in parallel.

2. The computer-implemented method according to claim 1, wherein predicting the anatomical labels of the anatomical structure based on the centerline of the anatomical structure, by utilizing a trained deep learning network further comprises:
   sampling the centerline to form a centerline graph of the anatomical structure, wherein each sampling point is a node of the centerline graph and each line segment on the centerline connecting each pair of adjacent nodes is an edge of the centerline graph; and
   predicting the anatomical labels of the anatomical structure based on the centerline graph, by utilizing the trained deep learning network.

3. The computer-implemented method according to claim 2, wherein the at least two branch networks include a first branch network and a second branch network, and predicting the anatomical labels of the anatomical structure based on the centerline graph, by utilizing the trained deep learning network further comprises:
   generating a geometric feature embedding of each node based on coordinate information of each node, by utilizing the first branch network;
   generating an image feature embedding of each node based on an image patch or an mask patch corresponding to each node, by utilizing the second branch network;
   generating a joint feature embedding of each node based on the geometric feature embedding and the image feature embedding, by utilizing the Graph Neural Network;
   generating an anatomical label corresponding to each node in the centerline graph based on the joint feature embedding, by utilizing the Recurrent Neural Network; and
   generating the anatomical labels of the anatomical structure based on the anatomical label corresponding to each node in the centerline graph, by utilizing the Probability Graph Model.

4. The computer-implemented method according to claim 3, wherein predicting the anatomical labels of the anatomical structure based on the centerline graph, by utilizing the trained deep learning network further comprises:
   dividing the centerline into a plurality of cells;
   after generating a joint feature embedding of each node by utilizing the Graph Neural Network, performing a cell level average pooling for the joint feature embedding of each node based on the divided cells of the centerline to generate cell level features;
   generating the cell level anatomical labels of the centerline graph based on the cell level features, by utilizing the Recurrent Neural Network; and
   generating the anatomical labels of the anatomical structure based on the cell level anatomical labels, by utilizing the Probability Graph Model.

5. The computer-implemented method according to claim 4, wherein the anatomical structure is a vessel, and each cell of the centerline corresponds to a vessel branch between two bifurcations of the vessel.

6. The computer-implemented method according to claim 3, wherein the first branch network is a point cloud neural network.

7. The computer-implemented method according to claim 3, wherein the second branch. network is a CNN, a RNN, or an MLP.

8. The computer-implemented method according to claim 3, wherein the Recurrent Neural Network is an LSTM, a GRU, a GLSTM, or a CGRU.

9. The computer-implemented method according to claim 2, wherein the edges of the centerline graph are directed edges.

10. The computer-implemented method according to claim 1, wherein the anatomical structure comprises at least one of a vessel, a respiratory tract, or a mammary duct.

11. The computer-implemented method according to claim 1, further comprising:
receiving training data comprising a sample anatomical structure with an extracted sample centerline or a sample medical image containing the sample anatomical structure with the extracted sample centerline and a ground truth of the anatomical labels of the sample anatomical structure; and
training the deep learning network by performing a joint optimization of model parameters of the at least two branch networks, the Graph Neural Network, the Recurrent Neural Network and the Probability Graph Model using the training data.

12. A system for generating anatomical labels of an anatomical structure, comprising:
an interface configured to receive an anatomical structure with an extracted centerline, or a medical image containing the anatomical structure with the extracted centerline; and
at least one processor configured to predict the anatomical labels of the anatomical structure based on the centerline of the anatomical structure, by utilizing a trained deep learning network, the deep learning network comprises a branched network, a Graph Neural Network, a Recurrent Neural Network and a Probability Graph Model which are connected sequentially in series, wherein the branched network comprises at least two branch networks in parallel.

13. The system according to claim 12, wherein to predict the anatomical labels of the anatomical structure based on the centerline of the anatomical structure, by utilizing a trained deep learning network, the at least one processor is further configured to:
sample the centerline to form a centerline graph of the anatomical structure, wherein each sample point is a node of the centerline graph and each line segment on the centerline connecting each pair of adjacent nodes is an edge of the centerline graph; and
predict the anatomical labels of the anatomical structure based on the centerline graph, by utilizing the trained deep learning network.

14. The system according to claim 13, wherein the at least two branch networks include a first branch network and a second branch network, and to predict the anatomical labels of the anatomical structure based on the centerline graph, by utilizing the trained deep learning network, the at least one processor is further configured to:

generate a geometric feature embedding of each node based on coordinate information of each node, by utilizing the first branch network;
generate an image feature embedding of each node based on an image patch or an mask patch corresponding to each node, by utilizing the second branch network;
generate a joint feature embedding of each node based on the geometric feature embedding and the image feature embedding, by utilizing the Graph Neural Network;
generate an anatomical label corresponding to each node in the centerline graph based on the joint feature embedding, by utilizing the Recurrent Neural Network; and
generate the anatomical labels of the anatomical structure based on the anatomical label corresponding to each node in the centerline graph, by utilizing the Probability Graph Model.

15. The system according to claim 14, wherein to predict the anatomical labels of the anatomical structure based on the centerline graph, by utilizing the trained deep learning network, the at least one processor is further configured to:
divide the centerline into a plurality of cells;
generate a joint feature embedding of each node by utilizing the Graph Neural Network, performing a cell level average pooling for the joint feature embedding of each node based on the divided cells of the centerline to generate cell level features;
generate the cell level anatomical labels of the centerline graph based on the cell level features, by utilizing the Recurrent Neural Network; and
generate the anatomical labels of the anatomical structure based on the cell level anatomical labels, by utilizing the Probability Graph Model.

16. The system according to claim 15, wherein the anatomical structure is a vessel, and each cell of the centerline is a vessel branch between two bifurcations of the vessel.

17. The system according to claim 14, wherein the first branch network is a point cloud neural network.

18. The system according to claim 14, wherein the second branch network is a CNN, a RNN, or an MLP.

19. The system according to claim 14, wherein the Recurrent Neural Network is an LSTM, a GRU, a GLSTM, or a CGRU.

20. A non-transitory computer-readable storage medium storing computer-executable instructions thereon, wherein the computer-executable instructions, when executed by a processor, cause the processor to perform a method for generating anatomical labels of an anatomical structure, the method comprising:
receiving an anatomical structure with an extracted centerline, or a medical image containing the anatomical structure with the extracted centerline; and
predicting, by at least one processor, the anatomical labels of the anatomical structure based on the centerline of the anatomical structure, by utilizing a trained deep learning network, wherein the deep learning network comprises a branched network, a Graph Neural Network, a Recurrent Neural Network and a Probability Graph Model, which are connected sequentially in series, wherein the branched network comprises at least two branch networks in parallel.

* * * * *